United States Patent [19]

Harrison et al.

[11] Patent Number: 5,434,313

[45] Date of Patent: Jul. 18, 1995

[54] ALDOLISATION-DEHYDRATION PROCESS

[75] Inventors: George E. Harrison, Billericay; Arthur J. Reason, Saltburn; Alan J. Dennis; Mohammad Sharif, both of Middlesbrough, all of England

[73] Assignee: Davy McKee (London) Limited, London, England

[21] Appl. No.: 313,298

[22] PCT Filed: Apr. 7, 1993

[86] PCT No.: PCT/GB93/00729

§ 371 Date: Oct. 6, 1994

§ 102(e) Date: Oct. 6, 1994

[87] PCT Pub. No.: WO93/20034

PCT Pub. Date: Oct. 14, 1993

[30] Foreign Application Priority Data

Apr. 7, 1992 [GB] United Kingdom ............... 9207756

[51] Int. Cl.⁶ .............. C07C 45/74; C07C 45/72; C07C 45/66; C07C 47/21
[52] U.S. Cl. .................. 568/461; 568/458; 568/463; 568/464; 568/465
[58] Field of Search ............ 568/458, 460, 461, 462, 568/463, 464, 465

[56] References Cited

U.S. PATENT DOCUMENTS 3,248,428  4/1966  Porter, Jr. et al. .............. 568/461
4,408,079 10/1983  Merger et al. ................. 568/461
4,943,663  7/1990  Diekhaus et al. ............... 568/461
5,243,081  9/1993  Ishino et al. .................. 568/463

FOREIGN PATENT DOCUMENTS 1036156  9/1953  France ........................... 568/461
 549006 11/1942  United Kingdom ............... 568/461
1010695 11/1965  United Kingdom ............... 568/461

Primary Examiner—Werren B. Lone
Attorney, Agent, or Firm—Rothwell, Figg, Ernst & Kurz

[57] ABSTRACT

An aldolisation-dehydration process is disclosed for converting an aldehyde, e.g. n-valeraldehyde, to a substituted acrolein, e.g. propyl butyl acrolein (2-propyl-hept-2-enal). Aldolisation and dehydration are effected in a stirred tank reactor (16; 111) using an alkali catalyst, such as sodium hydroxide. A reaction product stream (23; 113) containing both organic and aqueous phases is distilled (in column 25; 123) to yield a heterogeneous azeotrope containing water and aldehyde. On condensation and phase separation the lower water layer (34; 150) can be discharged from the plant without the need for neutralisation. From the bottom of the distillation zone a mixture (36;157) of substituted acrolein and alkali catalyst solution is obtained. The substituted acrolein is recovered as product (45;173), while the catalyst solution (47;175) is recycled to the aldolisation reactor. Part (49; 181) of the catalyst solution is purged to control the level of Cannizzaro reaction products.

45 Claims, 2 Drawing Sheets

ALDOLISATION-DEHYDRATION PROCESS

This application is a 371 of PCT/GB93/00729, filed Apr. 7, 1993.

This invention relates to a process for the production of unsaturated aldehydes by aldolisation followed by dehydration.

Aldolisation is a well known process in which aldehydes undergo dimerisation, typically in the presence of an alkali metal hydroxide catalyst, according to the following equation:

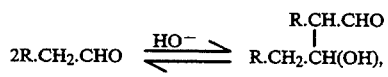   (1)

where R is a hydrogen atom, an alkyl group or an aryl group. This aldol can then undergo dehydration to form an unsaturated aldehyde which has twice as many carbon atoms as the starting aldehyde of formula $R.CH_2.CHO$, according to the following equation:

   (2)

For example, n-butyraldehyde forms ethyl propyl acrolein (2-ethylhex-2-enal) by the reactions:

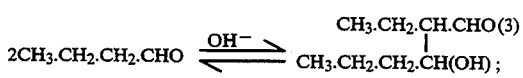   (3)

and

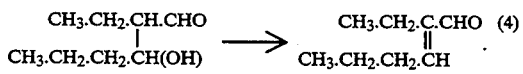   (4)

This reaction is commercially practised on a large scale as part of a process for production of the tonnage chemical, 2-ethylhexanol. This can be obtained by hydrogenation of ethyl propyl acrolein:

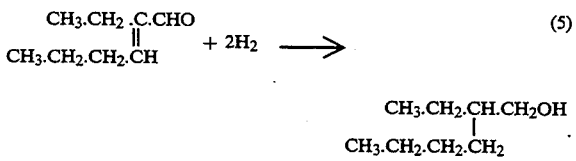   (5)

This alcohol, i.e. 2-ethylhexanol, is widely used as a plasticiser alcohol for the production of di-(2-ethylhexyl)phthalate which is a plasticiser in common use for plasticising polyvinyl chloride.

Plasticiser alcohols have to satisfy stringent purity criteria, including low acidity, low water content, lack of colour, and low "sulphuric acid colour". In this last mentioned test a sample of the plasticiser alcohol is reacted with concentrated sulphuric acid and the colour of the resulting solution is measured against a set of standard solutions, using visual or instrumental methods.

In the presence of an iso-aldehyde a mixed aldol product can be formed. For example, iso-butyraldehyde can react with n-butyraldehyde as follows:

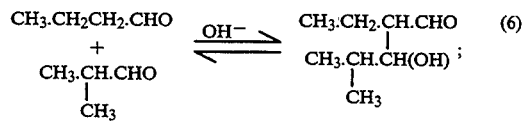   (6)

and

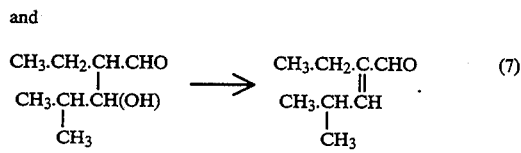   (7)

For a description of the mechanism of the aldolisation reaction reference may be made, for example, to the textbook "Organic Chemistry" by I. L. Finar, Second Edition, published by Longmans (1954), and to pages 127 and 128 thereof in particular.

A competing reaction to aldolisation is the Cannizzaro reaction:

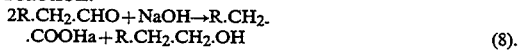   (8).

Since higher molecular weight aldehydes, such as n-butyraldehyde, and aqueous solutions have limited mutual solubility, the aldolisation reaction is a two phase liquid reaction. Presumably aldehyde undergoes mass transfer into the aqueous phase, and rapidly aldolises in the aqueous phase, and then the aldolisation products transfer back into the organic phase.

Various authors have studied the kinetics of aldolisation, including:

(1) P. Beltrame et al, La Chemica e L'Industria, 1973, 55, page 785 et seq.;
(2) P. Beltrame, Chemica e Industria, 1958, 40, page 533;
(3) T. Inoto & K. Aotani, Nippon Kagaku Zasshi, 1968, 89, page 240 (see also Chem. Abs. 1968, 69, 85912); and
(4) S. E.. Rudakova & VV Zarkov, Zh. Obshch. Khim., 1963, 33, page 3617 (see also Chem. Abs. 1964, 60, 7833).

A typical current design of aldolisation plant for production of ethyl propyl acrolein from n-butyraldehyde involves three reaction stages connected in series. The first reaction stage comprises a pumped loop in which fresh n-butyraldehyde is mixed with recycled material and make up quantities of sodium hydroxide solution and then pumped in turn through a static mixer and a cooler. Most of the reaction mixture is recycled but a portion is taken to the second stage. The reaction temperature in the first stage is 120° C. and the residence time is about 10 minutes. In the second stage the temperature is again 120° C. and the residence time is about 20 minutes. This second stage consists of a tank reactor through which is circulated by an external pump a mixture of organic and aqueous phases. The third stage is similar to the second stage. Material drawn off from the third stage is fed to a settler from which the upper organic phase comprising ethyl propyl acrolein is recovered for hydrogenation, whilst the lower aqueous phase is recycled to the first stage. A purge stream is taken from this aqueous recycle stream in order to remove the water formed in the process and to control the level of sodium n-butyrate, formed as a result of the Cannizzaro reaction, in the circulating aqueous liquor. This purge stream presents an environmental problem since the sodium hydroxide present in it must be neutralised and the neutralised stream subjected to biological treatment to reduce its biological oxygen demand (BOD), before it can be discharged to a watercourse. Other designs of aldolisation reactor use a plug flow reactor, in which the aqueous and organic phases flow together through a long narrow pipe which may be packed with static phase-mixing devices, such as Raschig rings, and which is usually surrounded with a heat exchange medium. In these designs the water produced in the aldolisation reactor is discharged from the reactor in the form of an aqueous alkaline solution. Thus the rate of removal of alkali from the plant is determined by the production of water in the aldolisation reaction rather than by chemical consumption of alkali as a result of the Cannizzaro reaction.

Although 2-ethylhexanol made from n-butyraldehyde is perhaps the most widely used plasticiser alcohol, it has more recently been proposed to use 2-propylheptanol made from n-valeraldehyde as an alternative thereto. The corresponding plasticiser, di-(2-propylheptyl) phthalate, is less volatile and less soluble in water and hence is likely to be more acceptable as a component of food packaging films, besides being less readily leached or otherwise lost from polyvinyl chloride articles plasticised therewith.

There is a need to provide an improved process for the production of unsaturated aldehydes by aldolisation and dehydration. In particular there is a need to provide a more environmentally friendly and efficient aldolisation process.

The present invention accordingly seeks to provide a novel, improved process for the production of unsaturated aldehydes by dimerisation of saturated aldehydes through aldolisation followed by dehydration of the resulting aldol. It further seeks to provide a process for aldolisation of saturated aldehydes followed by dehydration to form an unsaturated aldehyde whereby the water released in the dehydration reaction can be purged from the process without need for a neutralisation step.

The invention provides a process for the production of substituted acroleins which comprises aldolisation of an aldehyde or a mixture of aldehydes in the presence of an effective amount of a water-soluble aldolisation catalyst followed by dehydration to form at least one substituted acrolein and water, recovering from the aldolisation/dehydration step a reaction mixture comprising unreacted aldehyde or aldehydes, water, aldolisation catalyst, and said at least one substituted acrolein, and distilling the reaction mixture to separate (i) an overhead fraction comprising unreacted aldehyde or aldehydes and water from (ii) a bottom fraction containing said aldolisation catalyst and said at least one substituted acrolein, recycling unreacted aldehyde or aldehydes of said overhead fraction to the aldolisation/dehydration step, and purging from the system a stream substantially free from said aldolisation catalyst and comprising water from said overhead fraction.

According to another aspect of the present invention there is provided a continuous process for aldolisation of an aldehyde followed by dehydration to form a substituted acrolein containing twice as many carbon atoms as said aldehyde, which process comprises:

(a) providing an aldolisation zone and a distillation zone;

(b) continuously supplying to the aldolisation zone an organic stream containing said aldehyde and an aqueous stream containing an alkali catalyst;

(c) maintaining said aldolisation zone under aldolisation and dehydration conditions effective for conversion of said aldehyde in the presence of said alkali catalyst to an aldolisation product with subsequent dehydration of said aldolisation product to form said substituted acrolein;

(d) recovering from said aldolisation zone a reaction product stream comprising mixed organic and aqueous phases;

(e) distilling said reaction product stream in said distillation zone;

(f) recovering overhead from said distillation zone a vaporous stream comprising unreacted aldehyde and water;

(g) condensing said vaporous stream;

(h) allowing the resulting condensate to separate into an upper organic phase and a lower water phase;

(i) purging at least a part of said lower water phase;

(j) recycling material of said upper organic phase to said aldolisation zone;

(k) recovering from a bottom part of said distillation zone a bottoms product comprising an organic phase rich in substituted acrolein and an aqueous phase containing said alkali catalyst;

(l) cooling said bottoms product;

(m) allowing said cooled bottoms product to separate into an upper organic phase rich in substituted acrolein and a lower catalyst containing phase;

(n) recycling material of said lower catalyst containing phase to said aldolisation zone; and (o) recovering said upper organic phase of step (m).

The invention further provides a process for the production of substituted acroleins which comprises contacting an aldehyde or mixture of aldehydes under aldolisation and dehydration conditions with an effective amount of an aldolisation catalyst thereby to form by aldolisation/dehydration a reaction mixture comprising unreacted aldehyde or aldehydes, aldols, water, aldolisation catalyst, at least one substituted acrolein, and "heavies", supplying resulting reaction mixture to an intermediate section of a distillation zone which further includes a higher temperature section below said intermediate section and also a lower temperature distillation section, maintaining distillation conditions in the higher temperature section effective for decomposition of aldols and "heavies" in the presence of the aldolisation catalyst, recovering aldehyde or aldehydes from the lower temperature section for recycle to the aldolisation/dehydration step, and recovering from the higher temperature section a bottoms fraction comprising substituted acrolein and aldolisation catalyst.

The invention thus proposes aldolisation of an aldehyde, followed by dehydration of the aldolisation product, to yield a substituted acrolein containing twice as many carbon atoms as the aldehyde, by a process which comprises contacting the aldehyde under aldolisation conditions with an alkali catalyst, feeding the resulting aldolisation product mixture comprising organic and aqueous phases to a distillation zone in which a heterogeneous azeotrope comprising aldehyde and water is separated as overhead product which is condensed and allowed to separate into an organic phase comprising aldehyde which is recycled to the aldolisation zone and a water phase, part of which is purged from the plant and part of which is recycled as a reflux stream to the distillation zone, while a bottom product comprising substituted acrolein and an aqueous alkali catalyst solution containing Cannizzaro reaction products is also recovered from the distillation zone and is cooled and separated into an acrolein product layer and a catalyst solution for recycle to the aldolisation zone.

In the process of the invention there can be used any aldehyde containing at least two α-hydrogen atoms or a mixture of such an aldehyde with an aldehyde containing a single α-hydrogen atom or no α-hydrogen atom. Examples of aldehydes containing at least two α-hydrogen atoms include acetaldehyde, propionaldehyde, n-butyraldehyde, n-valeraldehyde, 3-methylbutyraldehyde, n-hexanal, β-henylacetaldehyde, n-heptanal, n-octanal, n-decanal, and the like. Examples of aldehydes containing a single α-hydrogen atom are 2-methylpropionaldehyde, 2-methylbutyraldehyde, 2-ethylhexanal, 2-methyl-3-phenylpropionaldehyde, and the like. Examples of aldehydes containing no α-hydrogen atoms are p-tolualdehyde, [2,2,2]-bicyclooctane-1-aldehyde, [2,2,1]-bicycloheptane-1-aldehyde, 1-methylcyclohexane-1-aldehyde, benzaldehyde, and the like.

It is preferred that the aldehyde is selected from aldehydes which contain from 3 to about 10 carbon atoms and mixtures thereof. Preferably the aldehyde comprises an aliphatic aldehyde, such as n-butyraldehyde, n-valeraldehyde, a mixture of n- and iso-butyraldehydes, or a mixture of n-valeraldehyde and one or more of 2-methylbutyraldehyde and 3-methylbutyraldehyde. A mixture of $C_4$ and $C_5$ aldehydes can be used, if desired.

The alkali catalyst preferably comprises an alkali metal or alkaline earth metal hydroxide, bicarbonate or carbonate, or a mixture of two or more thereof. Since water is a product of the dehydration reaction, the alkali catalyst is normally present in the aldolisation zone in aqueous solution. Preferably the alkali catalyst is selected from sodium hydroxide, sodium carbonate, potassium hydroxide, potassium carbonate, or a mixture of two or more thereof. Other suitable aldolisation catalysts include lithium, rubidium and caesium hydroxides and carbonates, and calcium, strontium and barium hydroxides.

The concentration of alkali catalyst in the aqueous phase in the aldolisation zone typically ranges from about 0.1% w/v up to about 5.0% w/v or more, e.g. up to about 10% w/v or higher. Under normal circumstances, however, the concentration of alkali catalyst in the aqueous phase ranges from about 0.1% w/v up to about 3% w/v.

Since the Cannizzaro reaction is a competing reaction which an aldehyde can undergo in the presence of the alkali catalyst, the aqueous phase will normally contain also an alkali metal or alkaline earth salt or salts of the organic acid or acids corresponding to the aldehyde or aldehydes used as starting material. Since the substituted acrolein may also undergo the Cannizzaro reaction, the aqueous phase may also contain an alkali metal or alkaline earth metal salt or salts of the organic acid or acids corresponding to the substituted acrolein or acroleins.

In step (n) of the process of the invention catalyst containing phase that has been recovered from a bottom part of the distillation zone is recycled to the aldolisation zone. As a result Cannizzaro reaction products can build up in this circulating catalyst-containing aqueous liquor to quite high levels, e.g. from about 5% w/v up to about 35% w/v or more. Steps are normally taken to prevent build up of excessive amounts of Cannizzaro reaction products in this aqueous liquor, as will be described further below. Hence it is preferred that the aqueous stream supplied to the aldolisation zone in step (b) comprises from about 0.1% w/v to about 5% w/v of sodium hydroxide and up to about 35% w/v of sodium salts of organic acids produced by Cannizzaro reactions.

The aldolisation zone is typically maintained at a temperature in the range of from about 65° C. up to about 80° C. or higher, preferably in the range of from about 80° C. to about 150° C. The operating pressure of the aldolisation zone can vary within fairly wide limits. This pressure is determined by the temperature and composition of the organic and aqueous phases in the aldolisation zone, if a vapour phase is present. If the aldolisation zone is full of liquid, then any desired pressure can be imposed. Operating pressures in the aldolisation zone typically range from about 0.1 bar up to about 20 bar or higher, e.g. from about 0.5 bar to about 10 bar.

Aldehyde is supplied to the aldolisation zone, in addition to aqueous alkali catalyst-containing solution. Such aldehyde can comprise feed aldehyde (or make up aldehyde) and recycled aldehyde. The ratio of recycled aldehyde to feed aldehyde can range, for example, from about 5:1 to about 1:50 by volume. Typically the ratio is from about 1:1 to about 1:20.

The aldehyde residence time in the aldolisation zone is typically from about 1 minute up to about 150 minutes or more, normally at least 2 minutes, e.g. from about 5 minutes to about 75 minutes.

In the aldolisation zone the organic and aqueous phases are dispersed one in the other. Generally any static or dynamic mixing method that provides the required degree of dispersion of the phases one in the other can be used.

The aldolisation zone may comprise a static mixing zone. Alternatively, however, it comprises a vessel, optionally fitted with internal baffles, fitted with an impeller. Since the rate of reaction appears to depend strongly upon the inter-phase area, due to the need for the aldehyde to cross the aqueous phase-organic phase interface in order to come into contact with the alkali catalyst, it is desirable to agitate the two phases vigorously so as to form a liquid-liquid dispersion. Preferably this liquid-liquid dispersion is an aqueous-continuous dispersion so that the dispersion is of the oil-in-water type. This can usually be achieved, when using an impeller, by ensuring that the impeller is in the aqueous phase at start up. Typically the power supplied to the impeller ranges from about 0.5 to about 5.0 kW/$m^3$ of liquor, e.g. from about 1.0 to about 3.0 kW/$m^3$ of liquor.

In the dispersion formed in the aldolisation zone the organic phase:aqueous phase ratio typically ranges from about 3:1 to about 1:15 by volume, e.g. from about 2:1 to about 1:4 by volume.

The distillation zone may be operated at a lower pressure than that prevailing in the aldolisation zone. Typically the distillation zone is operated at a pressure of from about 0.01 bar up to about 10 bar, e.g. from about 0.1 bar up to about 2 bar.

In the distillation zone a heterogeneous azeotrope or mixture of azeotropes comprising water and unreacted aldehyde or aldehydes is recovered overhead and is condensed. Preferably the distillation conditions are selected so as to permit a minor amount of substituted acrolein to appear in the overhead vapour stream from the distillation zone and in the resulting condensate. In this way it is assured that any alcohol formed by Cannizzaro reactions is removed from the upper part of the distillation zone. The resulting condensate is allowed to separate into two phases. The upper organic phase contains mainly aldehyde or aldehydes and most or all of this is recycled to the aldolisation zone. Part of this upper organic phase can be purged from the plant in order to limit the build up of chemically inert low boiling materials. Such materials are typically non aldehyde materials and may include an alcohol or alcohols produced by the Cannizzaro reaction. Other compounds may be formed by very minor by-product reactions or may have entered the plant as minor contaminants of the feed aldehyde stream. The lower aqueous layer is essentially water saturated with aldehyde or aldehydes. Part of this lower aqueous layer, and optionally some of the upper organic phase, is recycled to the distillation zone to form a reflux stream. The remainder is purged from the plant. Since it contains no alkali catalyst, it is not necessary to neutralise this stream prior to discharge to a water course.. However, in order to minimise loss of aldehyde from the plant and to reduce biological oxygen demand of the stream prior to discharge, it can be stripped with steam. The vapours from this steam stripping step, which contain recovered volatile organic materials, can be admixed with the vaporous heterogeneous azeotrope recovered from the distillation zone and condensed together therewith. The stripped aqueous stream can then be further treated, prior to discharge, in order to reduce its biological oxygen demand and chemical oxygen demand to a still lower level.

If necessary, part of this lower aqueous layer from the heterogeneous azeotrope condensate can be recycled to the aldolisation zone to maintain the water balance therein.

From a bottom part of the distillation zone there is recovered a hot mixture of substituted acrolein and aqueous phase containing alkali catalyst (and Cannizzaro reaction products). Part of this hot mixture is cooled and allowed to separate into two layers, while the rest can be recycled through a reboiler to the distillation zone. The two layers obtained on cooling the hot mixture from a bottom part of the distillation zone are separated. The upper organic layer comprises substituted acrolein product which can be passed on for further purification or storage or direct to a hydrogenation unit for conversion to the corresponding alcohol, which is typically a $C_8$ or $C_{10}$ plasticiser alcohol such as 2-ethylhexanol or 2-propylheptanol.

The lower layer separated from the substituted acrolein layer comprises an aqueous solution of alkali catalyst and Cannizzaro reaction products. Part of this is preferably purged from the plant to control the build up of Cannizzaro reaction products in the circulating aqueous liquor whilst the remainder is recycled to the aldolisation zone. Fresh alkali catalyst is desirably admixed with this recycled aqueous liquor to compensate for the alkali metal or alkaline earth metal ions lost in the purge stream.

Throughout this specification and claims, unless otherwise specified, all percentages are based on 100 moles of feed aldehyde.

In order that the invention may be clearly understood and readily carried into effect a first preferred process in accordance therewith will now be described, by way of example only, with reference to the accompanying FIG. 1 which is a flow diagram of a plant for the continuous production of propyl butyl acrolein (2-propylhept-2-enal) from n-valeraldehyde.

BRIEF DESCRIPTION OF THE DRAWING

It will be appreciated by those skilled in the art that, as the drawing is diagrammatic, many items which would be required in accordance with conventional practice on a commercial plant, such as valves, pressure control valves, temperature sensors, pressure sensors, temperature controllers, pressure controllers, pumps, coolers, heat exchangers, and the like, have been omitted for the sake of clarity. The provision of such conventional items of equipment forms no part of the present invention. Such items would be fitted in accordance with normal chemical engineering practice.

Figure 1:
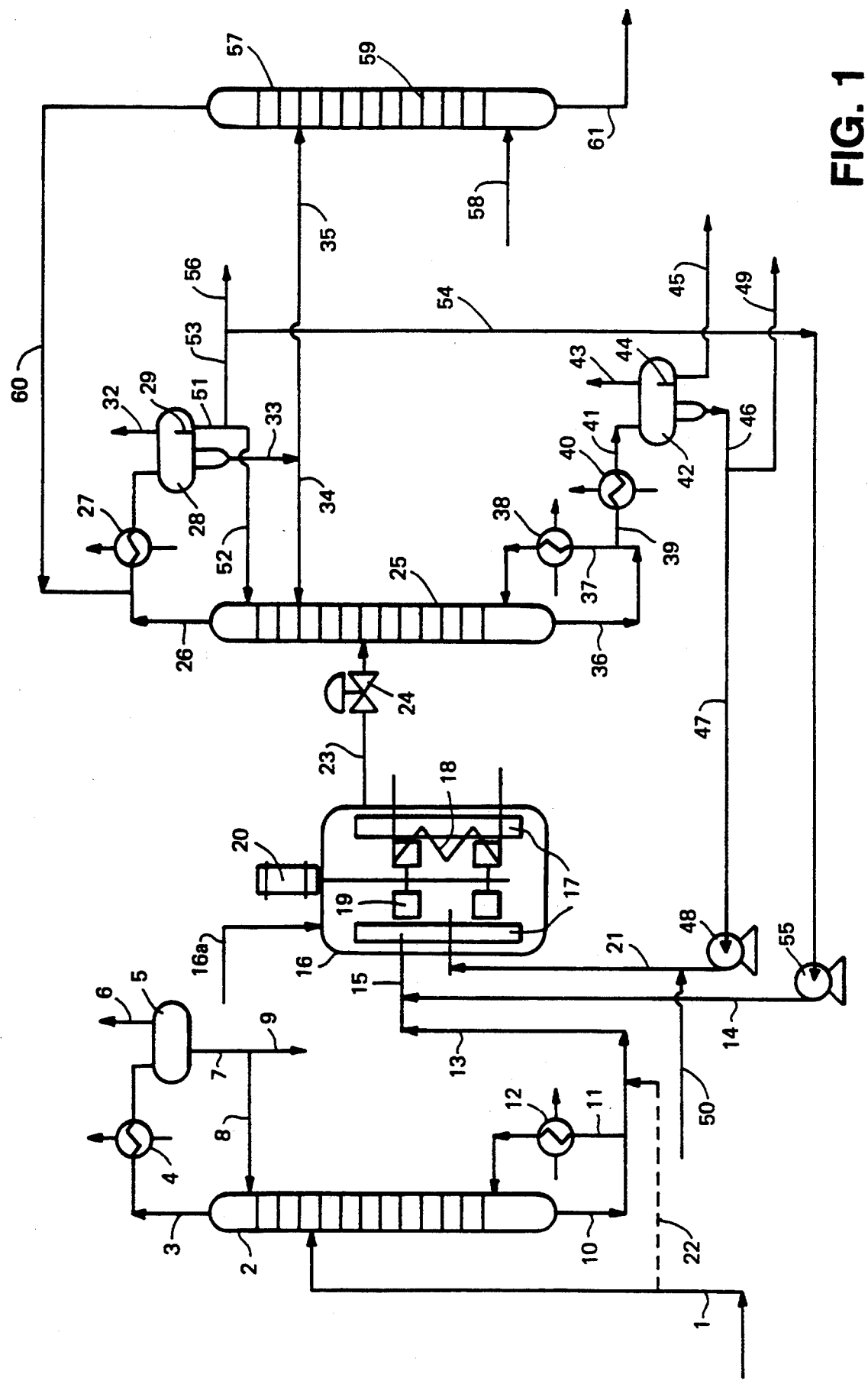
Referring to FIG. 1, a feed supply of a mixture of $C_5$-aldehydes is fed to the plant in line 1. This mixture of $C_5$-aldehydes is produced by hydroformylation of butene-1 or a mixture of $C_4$ olefins and contains a major proportion, typically 95 molar % or more, of n-valeraldehyde, with the balance comprising mainly iso-valeraldehyde (2-methylbutyraldehyde), lesser amounts of 3-methylbutyraldehyde, and a trace only, typically less than 0.001 molar %, of 2,2-dimethylpropionaldehyde. This is fed to a distillation column 2. A vaporous mixture comprising iso-valeraldehyde is recovered overhead in line 3 and is condensed by means of condenser 4. Condensate is collected in a condensate vessel 5 which has a vent line 6. Condensate is drawn off from vessel 5 in line 7; part of the stream in line 7 is recycled as reflux stream to the top of column 2 in line 8 while the remainder is passed to storage in line 9. The rate of withdrawal of condensate in line 9 can be varied so as to reduce the proportion of iso-valeraldehyde in the bottom product from distillation column 2 to as low a level as possible or to adjust the proportion of iso-valeraldehyde and any other $C_5$ aldehyde constituent in that bottom product to a desired level.

A stream of n-valeraldehyde is recovered from the bottom of column 2 in line 10; part is recycled to the column in line 11 through column reboiler 12. The remainder passes on in line 13 for admixture with a recycle stream from line 14. The resulting mixed stream in line 15 then enters an aldolisation reactor 16. This comprises a tank fitted with internal baffles 17, a cooling coil 18 and an agitator 19 driven by a motor 20. It is maintained at 120° C. and at a pressure of 4.2 bar. Aldolisation reactor 16 is also fed from line 21 with a stream of an aqueous liquor containing 2% w/v sodium hydroxide as well as up to 30% w/v of sodium salts of organic acid formed by Cannizzaro reactions.

If the n-valeraldehyde feedstock is sufficiently pure, or if the presence of isomeric products in the propyl butyl acrolein product can be tolerated, then distillation column 2 can be omitted. In this case the feedstock can be fed directly to line 13 via line 22.

In aldolisation reactor 16 the n-valeraldehyde feedstock undergoes aldolisation and dehydration according to the following equations:

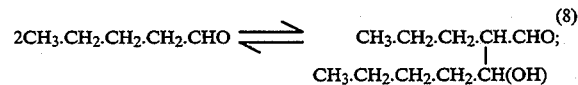
(8)

and

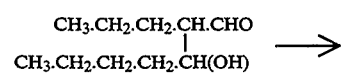

-continued

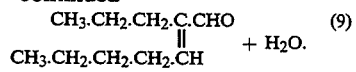

If the feedstock contains also iso-valeraldehyde (2-methylbutyraldehyde), then this can condense with n-valeraldehyde as follows:

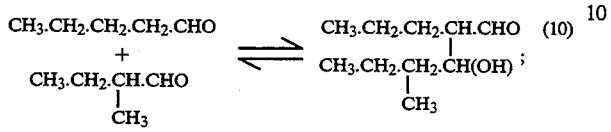

and

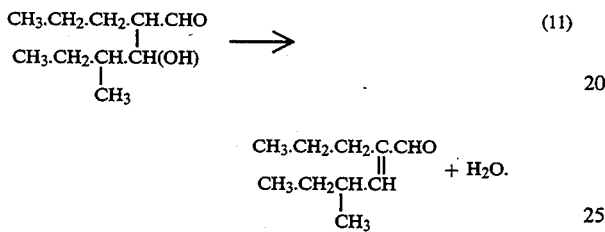

It is well known that the first stage of the aldolisation reaction (e.g. equation (8)) is reversible in the presence of the alkali catalyst. The reaction that eliminates water (e.g. equation (9)) is essentially irreversible and depends on the elimination of water in the form of the hydroxy group in the 3-position of the primary aldol adduct and a hydrogen atom from the 2-position of the primary aldol adduct. However, iso-valeraldehyde cannot aldolise with itself and then form an unsaturated aldehyde by dehydration nor can the primary aldol product made by reaction of iso-valeraldehyde and n-valeraldehyde according to equation (12):

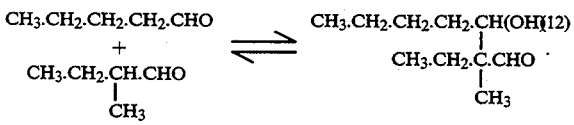

This is because these primary aldol adducts do not contain a hydrogen atom in the 2-position (i.e. an α-hydrogen atom). Therefore those primary aldol adducts not possessing α-hydrogen atoms are in dynamic equilibrium with $C_5$ aldehydes in the presence of the alkali catalyst, and the resulting regenerated $C_5$ aldehydes can then realdolise with a different partner aldehyde to form aldols which do contain α-hydrogen atoms and can subsequently dehydrate to form dehydrated aldol products. If the feedstock also contains 3-methylbutyraldehyde, then this can form a further series of isomeric aldolisation and dehydration products by self dimerisation and by forming aldolisation dimers with n-valeraldehyde or iso-valeraldehyde. Again, any primary aldol adducts formed (e.g. by reaction with 2-methylbutyraldehyde) that do not contain a-hydrogen atoms will be in equilibrium with the original reactants when in the presence of the alkali catalyst. Hence further minor components of the unsaturated dimeric aldehyde product in line 21 may include:

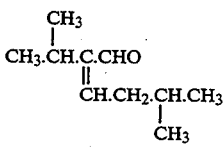

(Reaction product of 3-methylbutyraldehyde with itself)

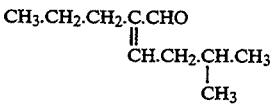

(Reaction product of 3-methylbutyraldehyde with n-valeraldehyde)

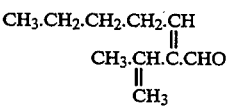

(Reaction product of n-valeraldehyde with 3-methylbutyraldehyde)

and

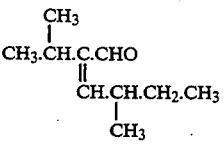

(Reaction product of 2-methylbutyraldehyde with 3-methylbutyraldehyde)

Typically at least 80%, preferably at least 90%, and even more preferably at least 95% or more (e.g. up to or more) of the feed aldehyde is converted to the desired dimeric unsaturated aldehyde product (i.e. substituted acrolein) in the process of the invention. The remainder is converted to more complex products containing 3,4 or more times as many carbon atoms per molecule as the starting aldehyde.

In practice it appears that n-valeraldehyde reacts about 6 times faster than 2-methylbutyraldehyde and is slightly less reactive than 3-methylbutyraldehyde.

The invention enables production of a $C_{10}$ substituted a acrolein mixture which comprises (i) at least 76 molar %, and preferably at least 88 molar % 2-propylhept-2-enal, (ii) not more than 20 molar % and preferably not more than 10 molar % 2-propyl-4-methylhex-2-enal, and (iii) not more than 4 molar % in total, and preferably not more than 2 molar % in total, of 2-propyl-5-methylhex-2-enal, 2-iso-propylhept-2-enal, 2-iso-propyl-5-methylhex-2-enal, and 2-iso-propyl-4-methylhex-2-enal. Preferably the $C_{10}$ substituted acrolein mixture comprises (i) at least 97.6 molar % 2-propylhept-2-enal, (ii) not more than 2.4 molar % 2-propyl-4-methylhex-2-enal, and (iii) not more than 0.01 molar % in total of 2-propyl-5-methylhex-2-enal, 2-iso-propylhept-2-enal, 2-iso-propyl-5-methylhex-2-enal, and 2-iso-propyl-4-methylhex-2-enal. It is preferred that the $C_{10}$ substituted acrolein mixture contains less than 0.5 molar % of, more preferably than 0.1 molar %, and even more preferably less than 0.03 molar %, of any material other than 2-propylhept-2-enal, 2-propyl-4-methylhex-2-enal, 2-propyl-5-methylhex-2-enal, 2-iso-propylhept-2-enal, 2-iso-propyl-5-methylhex-2-enal, and 2-iso-propyl-4-methylhex-2-enal.

It is desirable, though not essential, that aldolisation reactor 16 is operated under aqueous-continuous conditions so that the organic phase is dispersed in the aqueous phase under the influence of the agitator 19.

Preferably a small flow of oxygen free permanent gas, such as nitrogen, is supplied in line 16 g to the vapour space of reactor 16 in order to provide a stable reactor pressure over a range of temperatures.

An aldolisation product stream consisting of a mixture of aqueous alkaline liquor and organic phase is removed from aldolisation reactor 16 in line 23 and passes through valve 24 to a further distillation column 25 which is operated substantially at atmospheric pressure. An azeotropic mixture comprising unreacted $C_5$ aldehyde or aldehydes and water is recovered overhead in line 26 and condensed by means of condenser 27. The condensate flows on to a condensate vessel 28 in which it separates into two layers.

Reference numeral 32 indicates a vent line for condensate vessel 28.

The lower phase in condensate vessel 28 is water, saturated with n-valeraldehyde together possibly with minor amounts of iso-valeraldehyde and 3-methylbutyraldehyde. Part is recycled to column 25 as a reflux stream via lines 33 and 34 whilst a purge stream is taken in line 35.

The bottom product from distillation column 25 comprises propyl butyl acrolein (2-propylhept-2-enal), in admixture with usually minor amounts of isomers thereof if the feed aldehyde to the aldolisation reactor 16 in line 13 also contains iso-valeraldehyde and/or 3-methylbutyraldehyde. The bottom product also contains an alkaline phase. This bottom product is recovered in line 36 from column 25. Part is recycled to column 25 in line 37 through column reboiler 38. The remainder passes in line 39 to a cooler 40 and thence in line 41 to a decanter vessel 42. This has a vent line 43 and an internal weir 44. The upper organic phase comprises 2-propylhept-2-enal (propyl butyl acrolein) and is passed forward for hydrogenation in line 45 after overflowing weir 44. The lower aqueous phase contains sodium hydroxide and is recycled to aldolisation reactor 16 via lines 46, 47 and 21 by means of pump 48. A purge stream is taken in Line 49 to control the amount of sodium salts of $C_5$ carboxylic acids, mainly n-valeric acid, formed as a result of Cannizzaro reactions. Since some sodium ions are lost in the purge stream in line 49 a corresponding amount of fresh sodium hydroxide liquor is supplied to line 21 by way of line 50.

The upper organic layer in condensate vessel 28 comprises unreacted n-valeraldehyde and, optionally, also minor amounts of iso-valeraldehyde and 3-methylbutyraldehyde, possibly together with traces of "lights" such as alkanes, overflows weir 29 and passes into line 51. Part may be recycled to column 25 in line 52 while the remainder flows in line 53. A major part of the flow in line 53 is recycled by way of line 54 and pump 55 to form the recycle stream in line 14. A minor part thereof can be purged from the plant in line 56 in order to limit any accumulation of "lights" in the plant.

The aqueous phase in line 35 is passed to a steam stripping column 57 which is supplied in line 58 with steam. Steam from line 58 flows upwardly through column 57 against the downward flow of aqueous phase and strips dissolved organic materials, such as n-valeraldehyde therefrom. Column 57 can contain trays 59 or packing as may be most expedient. A mixture of steam and minor amounts of organic materials is recovered overhead from column 57 in line 60 and is mixed with the vapours in line 26 to be condensed in condenser 27. Stripped aqueous phase is recovered from the bottom of column 57 in line 61 and is passed forward to an optional further treatment stage (not shown) to reduce its chemical oxygen demand (COD) and its biological oxygen demand (BOD) prior to disposal.

If desired the alkali purge stream in line 49 can also be subjected to steam stripping prior to neutralisation and disposal. This will normally be carried out in a separate steam stripping column from column 57. However, the purge stream in line 49 can, if desired, be mixed with the stream in line 35 and fed also to column 57. In this case the stream in line 61 is neutralised prior to the aforementioned treatment to reduce its COD and BOD.

It will be appreciated by those skilled in the art that the illustrated plant can be used with equal success for effecting aldolisation of other aldehydes and the subsequent dehydration of the aldolisation products. Thus the n-valeraldehyde-containing feed in line 1 can be replaced by propionaldehyde, by n-butyraldehyde or an n-/iso-butyraldehyde mixture, by n-hexanal, by n-heptanal, or by n-decanal, or by a mixture of two or more of these aldehydes.

The invention is further illustrated by the following Examples.

EXAMPLE 1

A 250 ml capacity Magnedrive (Trade Mark) vessel manufactured by Autoclave Engineers was fitted with four 10% internal baffles and a variable speed stirrer. A liquid exit pipe of 2 mm internal diameter projected down into the vessel to a level such that the liquid capacity of the vessel was 180 ml. The continued removal of liquid from the vessel was effected by passing a low flow of nitrogen into the head space of the vessel thereby aiding the removal of liquid up the exit pipe by a "gas lift" effect. Aldehyde and aqueous sodium hydroxide were pumped in at the desired rates from nitrogen purged reservoirs using reciprocating piston pumps. The two phase liquid stream emerging from the reactor was cooled, collected and discharged at intervals for analysis. Nitrogen was supplied on demand to the product vessel to prevent reactor pressure surges when discharging the collected material. The reactor exit line was fitted with an upstream pressure controller to set the overall pressure in the apparatus. The organic phase of the product mixture was filtered through hydrophobic paper to remove aqueous phase mist and stored under nitrogen to prevent oxidation and contamination by sodium compounds of the injector port of the gas-liquid chromatograph used to analyse the product. For long term storage the organic product was additionally washed with a small quantity of deionised water.

The reactor was heated by immersion in a thermostatically controlled oil bath. The stirrer speed was 1400 r.p.m. At start up the stirrer was positioned in the vessel so that it was in the aqueous phase. Hence the apparatus was operated under "aqueous phase continuous" conditions with an oil-in-water type dispersion being formed in the vessel under the influence of the stirrer. Using n-butyraldehyde as the feed aldehyde the results set out below in Table 1 were obtained.

TABLE 1

| N₂ flow (ml/min.) | Temp (°C.) | Obs. reaction rate (gMol/l/hr) | Res. Time (Min.) | % NaOH (w/v) | [O/A] | Product NBAL | (wt %) EPA |
|---|---|---|---|---|---|---|---|
| 40 | 120 | 16.65 | 25.71 | 2.00 | 1.8 | 2.04 | 94.24 |
| 40 | 120 | 16.52 | 25.71 | 1.00 | 1.8 | 2.85 | 93.63 |
| 40 | 120 | 16.31 | 25.71 | 0.50 | 1.8 | 4.05 | 92.69 |
| 40 | 120 | 8.32 | 51.43 | 1.00 | 1.8 | 2.06 | 94.04 |
| 40 | 120 | 16.51 | 25.71 | 1.00 | 1.8 | 2.88 | 93.74 |
| 40 | 120 | 32.55 | 12.86 | 1.00 | 1.8 | 4.22 | 92.68 |
| 4 | 120 | 8.35 | 51.43 | 1.00 | 1.8 | 1.77 | 94.36 |
| 40 | 120 | 16.52 | 25.71 | 1.00 | 1.8 | 2.83 | 93.70 |
| 40 | 120 | 16.31 | 25.71 | 0.50 | 1.8 | 4.05 | 92.89 |
| 40 | 120 | 15.98 | 25.71 | 0.25 | 1.8 | 5.98 | 89.27 |
| 4 | 63 | 16.14 | 25.71 | 2.00 | 1.8 | 5.08 | 89.05 |
| 4 | 83 | 16.49 | 25.71 | 2.00 | 1.8 | 3.01 | 94.64 |
| 4 | 104 | 16.62 | 25.71 | 2.00 | 1.8 | 2.25 | 94.64 |
| 4 | 83 | 16.45 | 25.71 | 2.00 | 1.8 | 3.21 | 93.91 |
| 4 | 103 | 16.62 | 25.71 | 2.00 | 1.8 | 2.25 | 94.26 |
| 40 | 120 | 16.66 | 25.71 | 2.00 | 1.8 | 1.99 | 94.38 |
| 4 | 120 | 16.69 | 25.71 | 2.00 | 1.8 | 1.84 | 94.62 |
| 4 | 120 | 8.39 | 51.43 | 2.00 | 1.8 | 1.27 | 94.66 |
| 4 | 120 | 16.69 | 25.71 | 2.00 | 1.8 | 1.81 | 94.70 |
| 4 | 120 | 33.07 | 12.86 | 2.00 | 1.8 | 2.71 | 93.85 |
| 4 | 120 | 21.36 | 25.71 | 2.00 | 5.0 | 3.08 | 93.27 |
| 4 | 120 | 19.36 | 25.71 | 2.00 | 3.0 | 2.40 | 93.74 |
| 4 | 120 | 16.69 | 25.71 | 2.00 | 1.8 | 1.81 | 94.70 |
| 4 | 120 | 13.03 | 25.71 | 2.00 | 1.0 | 1.44 | 94.42 |

Notes:
1. The N₂ flow is the nitrogen flow rate to the reactor head space
2. [O/A] indicates organic phase:aqueous phase ratio by volume (i.e. the feed n-butyraldehyde:feed aqueous NaOH solution volume ratio).
3. The balance of the product to 100% is "heavies", i.e. higher boiling materials than EPA.
4. EPA is ethyl propyl acrolein, i.e. 2-ethylhex-2-enal.
5. NBAL is n-butyraldehyde.

EXAMPLE 2

The apparatus used in Example 1 was used to investigate aldolisation and subsequent dehydration of the aldolisation product using a C₅-aldehyde feed stream which contained 0.9% 3-methylbutyraldehyde, 3.56% 2-methylbutyraldehyde and 94.81% n-valeraldehyde. At 120° C., with an N₂ flow rate of 40 ml/minute, and with the stirrer at 1400 r.p.m., the results obtained in Table 2 were obtained.

The results of further investigations with MBAL/N-VAL mixtures are given in Table 3 where the effect of reactor residence time, organic to aqueous ratio, sodium hydroxide concentration, reaction temperature and phase continuity were investigated. Feed 1 contained 13.26% 2MBAL and 0.04% "heavies" with the balance being NVAL. Feed 2 contained 12.21% 2MBAL, 0.06% "heavies, and 0.01% "lights" with the balance being NVAL.

TABLE 2

| Residence time (minutes) | [O/A] | NaOH concn. (g/l) | NaOH loss (%) | 3MBAL in product (%) | 2MBAL in product (%) | NVAL in product (%) | 2xVAL in product (%) | 3xVAL in product (%) | PBA in product (%) |
|---|---|---|---|---|---|---|---|---|---|
| 25.72 | 5:1 | 19.44 | 17.3 | 0.16 | 2.28 | 10.43 | 2.84 | 1.38 | 80.99 |
| 25.72 | 3:1 | 19.44 | 11.7 | 0.15 | 2.07 | 8.98 | 3.20 | 1.39 | 82.47 |
| 25.72 | 1.8:1 | 19.44 | 10.4 | 0.13 | 1.96 | 7.98 | 3.39 | 1.42 | 83.30 |
| 51.4 | 1.8:1 | 20.96 | 8.6 | 0.09 | 1.62 | 5.44 | 4.04 | 1.57 | 85.35 |
| 51.4 | 1.47:1 | 16.88 | 4.0 | 0.04 | 1.33 | 1.67 | 5.09 | 1.71 | 88.48 |
| 51.4 | 1.47:1 | 16.16 | 2.8 | 0.00 | 1.12 | 0.92 | 4.85 | 1.79 | 89.35 |
| 12.86 | 1.8:1 | 19.44 | 9.8 | 0.18 | 2.16 | 11.02 | 2.93 | 1.36 | 80.54 |
| 25.72 | 1.8:1 | 19.44 | 9.5 | 0.14 | 1.94 | 7.79 | 3.39 | 1.43 | 83.44 |
| 51.4 | 1.8:1 | 19.44 | 9.1 | 0.09 | 1.63 | 5.13 | 4.15 | 1.53 | 85.58 |

Notes to Table 2:
1) 3MBAL = 3-methylbutyraldehyde
2) 2MBAL = 2-methylbutyraldehyde
3) NVAL = n-valeraldehyde
4) 2xVAL = aldol product of 2MBAL and NVAL, e.g. 2-propyl-4-methylhex-2-enal
5) 3xVAL = aldol product of 3MBAL and NVAL, e.g. 2-propyl-5-methylhex-2-enal
6) PBA = propylbutylacrolein (2-propylhept-2-enal).
7) NaOH loss % is defined as that percentage amount of sodium hydroxide lost by the formation of Cannizzaro reaction products, e.g. sodium valerate, per pass.
8) [O/A] = organic phase:aqueous phase ratio by volume.

TABLE 3

| Residence Time (minutes) | [O/A] | NaOH Concn (g/l) | 2 MBAL in Product (%) | NVAL in Product (%) | 2xVAL in Product (%) | PBA in Product | Reactor Temp. (°C.) | Phase Continuity | Feed |
|---|---|---|---|---|---|---|---|---|---|
| 15 | 1.8 | 19.84 | 10.03 | 15.89 | 5.61 | 67.59 | 120 | Aqueous | 1 |
| 30 | 1.8 | 19.84 | 9.41 | 11.99 | 6.96 | 70.82 | 120 | " | 1 |
| 60 | 1.8 | 19.84 | 8.41 | 8.02 | 9.08 | 73.42 | 120 | " | 1 |

TABLE 3-continued

| Residence Time (minutes) | [O/A] | NaOH Concn (g/l) | 2 MBAL in Product (%) | NVAL in Product (%) | 2xVAL in Product (%) | PBA in Product | Reactor Temp. (°C.) | Phase Continuity | Feed |
|---|---|---|---|---|---|---|---|---|---|
| 18 | 1.0 | 19.36 | 8.14 | 10.88 | 7.06 | 73.23 | 120 | " | 2 |
| 30 | 1.0 | 19.84 | 8.49 | 8.33 | 8.72 | 73.64 | 120 | " | 1 |
| 60 | 1.0 | 19.36 | 6.58 | 5.43 | 10.51 | 76.28 | 120 | " | 2 |
| 30 | 1.0 | 19.36 | 8.96 | 11.52 | 6.67 | 72.08 | 107 | " | 2 |
| 30 | 1.0 | 19.36 | 8.66 | 16.07 | 4.89 | 69.12 | 88 | " | 2 |
| 30 | 1.0 | 9.82 | 8.47 | 11.09 | 6.65 | 72.95 | 120 | " | 2 |
| 30 | 1.0 | 38.88 | 7.07 | 6.73 | 9.78 | 75.42 | 120 | " | 2 |
| 30 | 0.5 | 19.84 | 6.69 | 5.74 | 10.33 | 76.26 | 120 | " | 2 |
| 30 | 3.0 | 19.84 | 10.06 | 15.18 | 5.77 | 68.19 | 120 | " | 1 |
| 30 | 1.8 | 19.36 | 8.56 | 11.77 | 6.67 | 72.14 | 120 | Organic | 2 |
| 30 | 3.0 | 19.36 | 9.53 | 16.80 | 5.07 | 67.66 | 120 | " | 2 |

Note to Table 3:
See the notes to Table 2 for the meanings of 2MBAL, NVAL, 2xVAL, PBA, and [O/A].

The results obtained with n-butyraldehyde (NBAL) (Table 1) show the effect of reaction temperature, reactor residence time, sodium hydroxide concentration, and organic phase to aqueous phase ratio [O/A] in the reactor on the amount of NBAL starting material in the reactor product. It is evident that under all conditions studied that a commercially significant amount of NBAL feed is present in the reactor product and that a process capable of recycling the unreacted feed aldehyde to the reaction zone is desirable.

The results obtained with the mixed $C_5$-aldehyde (i.e. n-valeraldehyde (NVAL), 2-methylbutyraldehyde (2MBAL) and 3-methylbutyraldehyde (3MBAL)) (Tables 2 and 3) show the effect of variation of O/A ratio, sodium hydroxide catalyst concentration, reaction temperature, and residence time on the amount of $C_5$-aldehydes in the reaction product; it is again evident that commercially significant amounts of $C_5$-aldehydes are unreacted and that a process capable of recycling the unreacted feed aldehydes to the reaction zone is desirable.

An additional important observation is that 2MBAL, present as a minor component in the feed, is still present to a significant extent in the product and forms a much higher proportion of the free $C_5$-aldehydes. Inspection of Tables 2 and 3 shows that the proportion of 2MBAL rises as the overall conversion of $C_5$-aldehydes increases. This effect is caused by the low reactivity of 2MBAL compared with the other aldehydes. Because 2MBAL must react with NVAL in order that a precursor to a $C_{10}$ plasticiser alcohol be formed it is especially advantageous that it is recovered from the reaction product (along with the other aldehydes) and returned to the reaction zone where reaction with NVAL or 3MBAL will lead to $C_{10}$ plasticiser alcohol precursors.

The experimental apparatus was accordingly modified to effect recovery and recycle of feed aldehydes from aldol reaction products, the recycle of the aqueous alkali catalyst and the recovery of the water reaction product as a separate stream.

Figure 2:
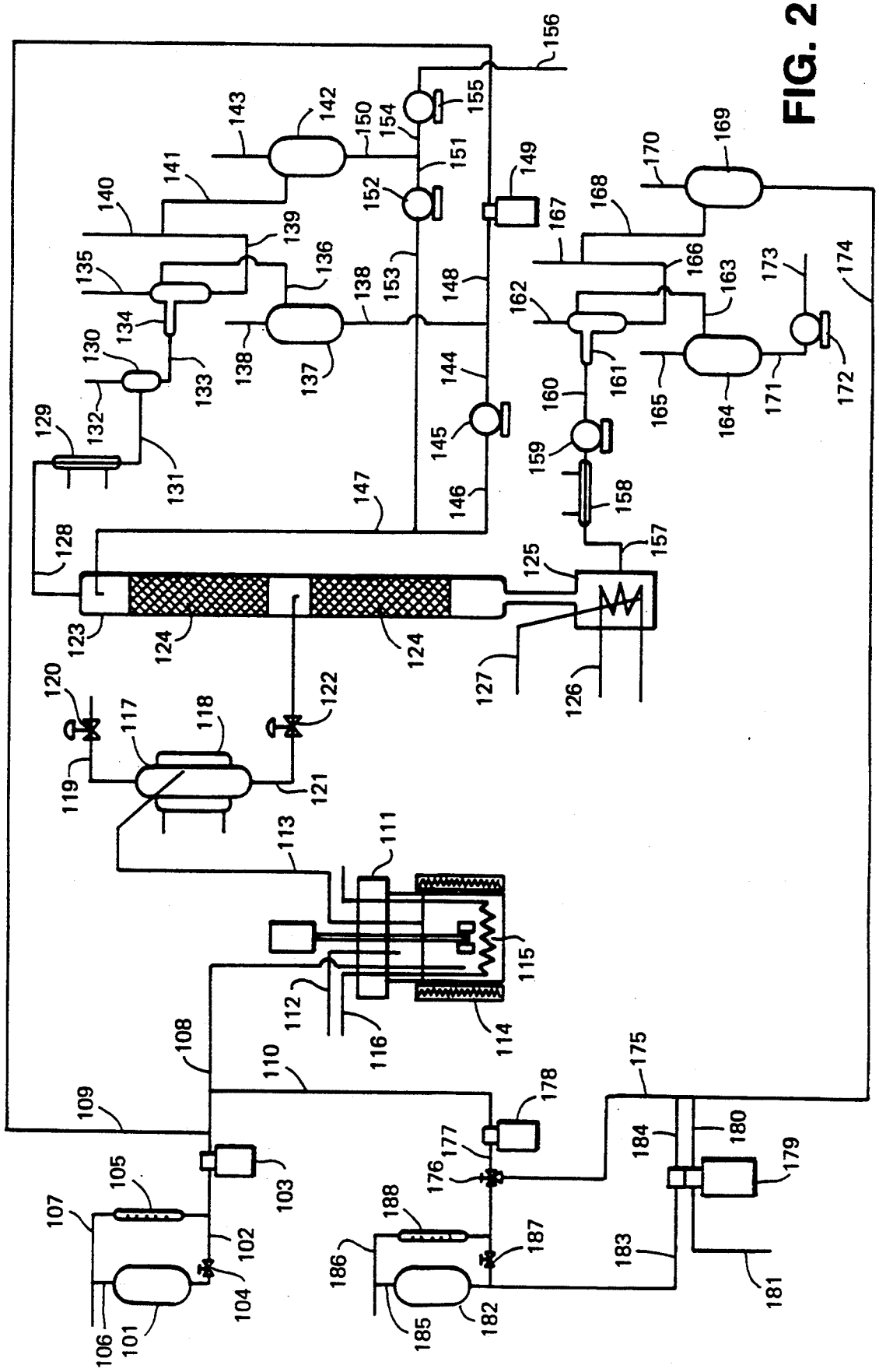

FIG. 2 is a flow diagram of an experimental rig for the continuous production of 2-ethylhex-2-enal from n-butyraldehyde or propyl butyl acrolein from n-valeraldehyde with recovery and recycle of feed aldehyde from the aldol reaction product zone to the aldolisation reactor zone.

Referring to FIG. 2, aldehyde feed from reservoir 101 passes by line 102 to precision feed pump 103 (the feed rate of pump 103 can be checked by closing valve 104 and measuring the flow with burette 105). Reservoir 101 is purged with a slow flow of oxygen-free nitrogen (not shown). The purge flow passes by lines 106 and 107 to a common vent (also not shown). The flow of feed aldehyde in line 108 is joined by recycle aldehyde from line 109 and an aqueous alkali stream from line 110. The mixture of aldehyde feed, recycle aldehyde and aqueous alkali continues in line 108 to aldolisation reactor 111. The operation of this reactor 111 is as described in Example 1; oxygen free nitrogen is supplied to the reactor ullage space by line 112 and the three phase fluid leaves the reactor by gas lift line 113.

The reactor nominal volume is 100 ml, while the liquid content can be varied from 30 ml to 70 ml by varying the position of the bottom of gas lift line 113. The reactor temperature is set by an external electrical heater 114 controlled by a thermocouple (not shown). Additional temperature control is provided by a cooling coil 115 (the aldol condensation reactions are exothermic). This coil is supplied by air through line 116 and enables fine control of the temperature of the reactor contents.

The three phase fluid passes through line 113 and enters a separating vessel 117 cooled by water jacket 118. The gas phase is separated from the liquid phase and passes via line 119 and control valve 120 to a common vent. Control valve 120 sets the upstream pressure in line 119 and thereby determines the overall reactor pressure. The liquids pass via line 121 and control valve 122 (setting the level in separating vessel 117) to distillation column 123.

Distillation column 123 contains two sections 124 of structured distillation packing; one above and one below the feed point of line 121 to the column 123. Each section 124 comprises twelve 25 mm diameter Sulzer ® distillation packing modules, each module having a height of 55 mm.

Column 123 is surrounded by four sections of "active insulation" (not shown) each section of which contains an internal heating element that automatically adjusts the insulation temperature to a temperature sensed at the column wall. Thus column 123 operates under conditions that are stable and close to adiabatic.

The column base is fitted with an oil heated reboiler 125. Hot oil is circulated through coil 126 from a thermostatically controlled oil bath (not shown). Line 127 is a capillary tube extending into the lower part of the reboiler cavity. A low flow of nitrogen passes through line 127 to establish smooth boiling and to protect the column 123 from oxygen ingress.

Column 123 operates substantially at atmospheric pressure, the pressure at the base being typically 10 to 50 cm water gauge (9.8 to 49.03 millibar) above atmospheric pressure.

Vapour leaves column 123 by line 128 and condenses in water cooled condenser 129 and passes into separator 130 via line 131. Nitrogen is vented by line 132 and the two phase liquid passes by line 133 to separator 134 (vented by line 135 to the common vent). The organic phase proceeds by overflow line 136 to surge vessel 137 (vented to the common vent by line 138) and the aqueous phase proceeds by line 139 past siphon breaker 140 (to common vent) and overflow line 141 to surge vessel 142 vented to the common vent by line 143.

The organic phase passes by lines 138 and 144 to pump 145 and line 146 and 147 to constitute the organic reflux to column 123; the excess flow passes by line 148 and pump 149 to return to the aldolisation reactor 111 via lines 109 and 108.

The aqueous phase passes by lines 150 and 151 to pump 152 and thence by lines 153 and 147 to constitute the aqueous reflux to column 123; the excess flow passes via line 154 and pump 155 to line 156. This alkali free stream (containing a small amount of dissolved organic materials) constitutes the net water made by the reaction system.

Two phase liquid leaves reboiler 125 by line 157 and is cooled in water cooler 158 and passes via pump 159 and line 160 to separator 161 (vented by line 162 to the common vent) where the two liquid phases separate. The speed of pump 159 is determined by a level sensor (not shown) in reboiler 125. The organic phase proceeds by overflow line 163 to surge vessel 164 (vented to the common vent by line 165) and the aqueous phase proceeds by line 166 past siphon breaker 167 (to common vent) and overflow line 168 to surge vessel 169 vented to the common vent by line 170.

The organic phase passes by line 171 to pump 172 and line 173 to nitrogen blanketed storage, this stream is the net organic product from the system.

The aqueous alkali phase passes by lines 174 and 175 to three way valve 176 and thence via line 177 to pump 178 and line 110 to constitute the aqueous phase recycle. A portion of the stream in line 174 can be withdrawn by pump 179 through line 180 and discharged from the system in line 181. This aqueous alkali discharge constitutes the aqueous purge from the system.

Pump 179 has a double head so that when it is discharging solution via lines 180 and 181 it is also supplying an equal volume of fresh alkali solution from reservoir 182 via lines 183 and 184 to line 175. Three way valve 176 can be set so that alkali solution can pass directly from reservoir 182 to line 110 to charge the system with fresh solution. In this case there is no flow in lines 175, 183 and 184 while pump 179 discharges the "old" solution via lines 180 and 181. Reservoir 182 is vented via lines 185 and 186 to the common vent. System valve 187 and burette 188 can be used to check the pumping rate of pump 178.

The control system operation is as follows:

a) aqueous alkali solution (recycle plus any make-up) is passed at a selected flow rate to the aldol reactor 111;

b) organic feed (made up from the available organic recycle and fresh organic feed) is also pumped to the aldol reactor 111 in a selected fixed ratio with respect to the total aqueous phase feed rate;

c) the net flow from the aldol reactor 111 passes via the gas separator 117 to the aldehyde recycle column 123;

d) since the vapour phase emerging from the top of the aldehyde recycle column 123 comprises a complex azeotropic mixture of water/feed aldehyde(s), water-/alcohol Cannizzaro reaction product(s) and water/substituted acrolein azeotropes, the column 123 is operated so that a little acrolein product (e.g. EPA or PBA) appears in the column overheads stream 128; this ensures that any low boiling by-product (e.g. pentanol or butanol, produced in the aldolisation reactor by the Cannizzaro reaction between aldehyde and sodium hydroxide) also appears in the column overheads stream 128 and does not accumulate in the column 123 where it could eventually cause surges in reflux rate;

e) organic reflux is returned at a set rate in lines 146 and 147, and water is returned as column reflux at a rate determined by the level of the aqueous phase in surge vessel 169; in this way the aqueous phase volume in the system is held constant;

f) organic column overhead in excess of that required by the reflux is recycled to the aldol reactor 111 via lines 109 and 108;

g) aqueous column overhead product in excess of that required by the system inventory balance is discharged from the system as the water product in line 156.

Whilst it is not intended that the validity of the present application shall be affected in any way by the accuracy or otherwise of the following explanation, it is believed that the compounds that are formed in the aldolisation reactor probably include a primary aldol which is formed from the feed aldehyde or aldehydes:

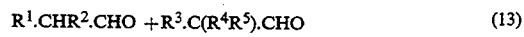
$$R^1.CHR^2.CHO + R^3.C(R^4R^5).CHO \qquad (13)$$

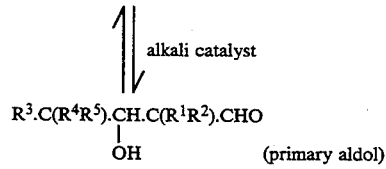

$$R^3.C(R^4R^5).CH.C(R^1R^2).CHO$$
$$| \qquad \text{(primary aldol)}$$
$$OH$$

in which $R^1$, $R^2$, $R^3$, $R^4$, and $R^5$ each represent independently of each other a hydrogen atom or an optionally substituted hydrocarbon radical. If $R^1$ or $R^2$ or both is or are a hydrogen atom, then water can be eliminated and the corresponding acrolein can be formed:

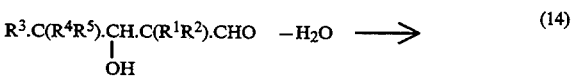
$$R^3.C(R^4R^5).CH.C(R^1R^2).CHO \quad -H_2O \longrightarrow \qquad (14)$$
$$|$$
$$OH$$

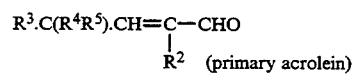
$$R^3.C(R^4R^5).CH=C-CHO$$
$$\qquad\qquad | $$
$$\qquad\qquad R^2 \quad \text{(primary acrolein)}$$

The primary aldol can also form a cyclic adduct with any aldehyde present:

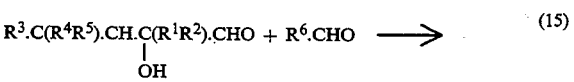
$$R^3.C(R^4R^5).CH.C(R^1R^2).CHO + R^6.CHO \longrightarrow \qquad (15)$$
$$\qquad | $$
$$\qquad OH$$

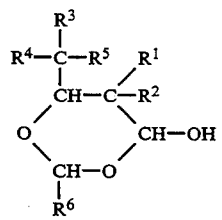

Thus, for example, when using a $C_5$ aldehyde feed, a $C_{10}$ primary aldol is first formed which can then react with a further molecule of aldehyde to form a cyclic $C_{15}$ compound. The compounds reported as aldols in the Examples that use a $C_5$ aldehyde feedstock are believed to be cyclic adducts formed by the addition of a $C_{10}$-primary aldol with a further molecule of a $C_5$ aldehyde, for example:

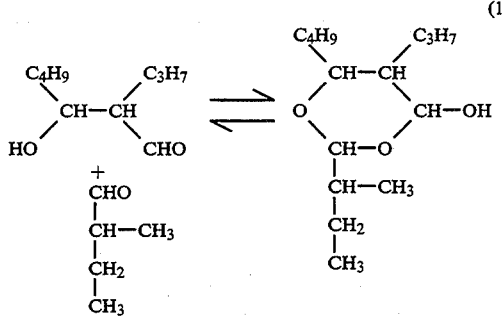

(16)

This is the cyclic adduct produced by the reaction of one molecule of 2-methylbutyraldehyde with the primary aldol produced by the reaction of two molecules of n-valeraldehyde. Isomeric compounds are formed by reaction of, for example, the same primary aldol with n-valeraldehyde or with 3-methylbutyraldehyde or by reaction of the isomeric primary aldol, which is formed between 3-methylbutyraldehyde and n-valeraldehyde, with any of the $C_5$ aldehydes present, i.e. n-valeraldehyde, 2-methylbutyraldehyde or 3-methylbutyraldehyde The number of possible ways that three different $C_5$ aldehyde molecules can react together to form a $C_{15}$ cyclic aldol adduct coupled with the number of possible geometrical isomers that can be formed by the substituted 1,3-dioxane ring structure provides a possible explanation of the multicomponent nature of the "aldol" peaks that are revealed by the gas-liquid chromatography (g.l.c.) recorder trace as a multiplet band.

The $C_{10}$ primary aldol product formed when using a $C_5$ aldehyde feedstock can also be postulated to react with the corresponding $C_{10}$ acrolein product to form a $C_{20}$ cyclic adduct:

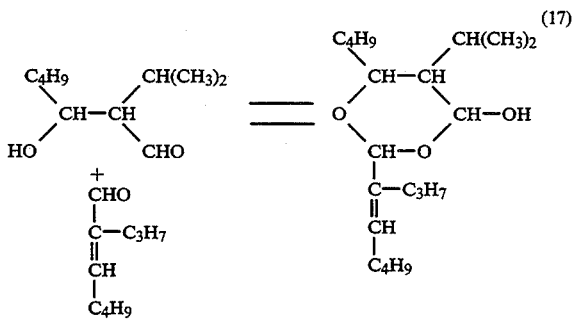

(17)

Similar $C_{20}$ cyclic adducts can be formed by analogous reactions if any other $C_5$ aldehyde is present. Such $C_{20}$ cyclic adducts can exist in many structural and geometrical isomers and this can account, at least in part, for the complex nature of the material named "heavies" that is found in the g.l.c. recorder traces.

In the apparatus of FIGS. 1 and 2 the portion of the distillation columns 25 and 123 below the entry point of the line 23 or line 123 respectively has an important function, namely decomposition of the cyclic adducts formed as by-products. In the presence of the aqueous phase alkali and under distillation conditions the $C_{15}$ aldols are in equilibrium with the $C_{10}$ primary aldol and $C_5$ aldehyde from which they are formed. Under such equilibrium conditions the $C_{10}$ primary aldol can eliminate water to form the desired $C_{10}$ substituted acrolein or it can revert back to two molecules of $C_5$ aldehyde. The overall function of this part of the distillation column is therefore to convert the $C_{15}$ aldols to $C_5$ aldehyde feed or $C_{10}$ substituted acrolein product. Similar reactions are postulated to be involved in the conversion of the $C_{20}$ cyclic adduct to $C_{10}$ substituted acrolein or $C_5$ aldehydes. Hence the lower portion of the distillation column 23 or 123 has an important role in directing the chemical reactions toward useful products.

The function of the upper part of the distillation column 23 or 123 is to separate the $C_5$ aldehydes for recycle to the aldolisation zone and retain the higher boiling materials so that they pass into the lower part of the distillation column.

The invention is further illustrated by the following Examples.

EXAMPLE 3

The reactor vessel 111 was supplied in line 102 with a virtually pure (99.8%) n-butyraldehyde (NBAL) feed at a feed rate of 116 ml/hr combined with recycled NBAL from line 109 at a feed rate of 30 ml/hr. The reactor was further supplied with aqueous feed having a sodium hydroxide concentration of 19.36 g/l and consisting of a combined flow of recycled material from line 174 and new feed material in line 184 at a combined rate in line 175 of 151 ml/hr. The total reactor liquid volume was 30 ml; this liquid was agitated by a Rushton ® turbine impeller in the aqueous phase region so as to provide a liquid dispersion of the oil-in-water type. Vortexing of the liquid mixture was controlled by one radial baffle having a radial dimension 10% of the diameter of the reactor vessel 111. The reactor temperature was maintained at 120° C. and reactor pressure was maintained at 140 p.s.i. (9.6 bar). The column head temperature at the top of distillation column 123 was 71° C. and the reboiler temperature in reboiler 125 was 97° C.

Aqueous sodium hydroxide solution (18.70 g/l) was purged from the system in line 181 at a rate of 80.50 ml/hr and substantially pure water was produced in line 150, for recycle to the column via line 153 or purge from the system via line 156, at a rate of 10.20 ml/hr. The results obtained during this run are shown in Table 4. These results were obtained using a gas-liquid chromatograph with a 0.3 mm internal diameter capillary column 25 m long containing a bonded phase (0.25-0.30 μm film thickness, equivalent to a silicone material OV1/SE30). The instrument was programmed to operate isothermally at 50° C. for 30 minutes after injection, followed by a temperature increase at 1° C./minute to 165° C. and then at 2° C./minute to 205° C., at which value the temperature was held constant until the end of the measurement. This analytical procedure, plus a rigorous avoidance of contamination of the instrument with acid or alkaline materials, enabled the analysis of aldol containing materials.

TABLE 4

| | Feed in line 102 | Aldol Reactor Product in line 121 | EPA Product in line 173 | Organic Recycle in line 138 |
|---|---|---|---|---|
| | Concentration % | | | |
| n-butyraldehyde | 99.80 | 7.81 | 0.22 | 86.45 |
| n-butanol | 0.10 | 0.05 | ND | 0.67 |
| Unknown | ND | 0.25 | 0.32 | 0.08 |
| Ethyl propyl acrolein | 0.10 | 83.73 | 97.53 | 12.79 |
| Aldols | ND | 4.87 | 0.14 | ND |
| Heavies | ND | 3.29 | 1.80 | ND |
| Lights | trace | trace | ND | trace |

ND = Not Detected

The column 123 was operated with a head temperature of 72.5° C., a feed temperature of 76.0° C., and a reboiler temperature of 97.2° C.

A comparison of the composition of the aldol reactor product in line 121 with that of the EPA product in line 173 clearly shows that the n-butyraldehyde has been removed (into the organic recycle stream in line 138) and that a major proportion of the aldols in the reactor product and a proportion of the heavy by-products have been converted into EPA product or recycled butyraldehyde.

EXAMPLE 4

The reactor vessel 111 was supplied in line 102 with n-valeraldehyde (NVAL) feed, containing a significant proportion of 2-methyl butyraldehyde (2MBAL) (ca. 5%), at a feed rate oft 107 ml/hr combined with recycled NVAL and 2MBAL in line 109 at a feed rate of 46 ml/hr. The reactor 111 was further supplied in line 175 with aqueous feed consisting of a combined flow of recycled aqueous material (with a sodium hydroxide concentration of 19.28 g/l) from line 174 and new feed material (with a sodium hydroxide concentration of 20.24 g/l) at a rate of 153 ml/hr from line 104. The total reactor liquid volume was 70 ml, the reactor temperature was maintained at 120° C. and reactor pressure was maintained at 140 p.s.i. (9.6 bar).

Organic reflux material was supplied to the aldehyde recycle column 123 via line 147 at a rate of 85 ml/hr. Aqueous reflux was supplied to the recycle column 123 via line 153 at a rate of 15 ml/hr. Recycled sodium hydroxide solution, with a sodium hydroxide content of 19.2 grams per liter, was purged from the system via line 181 at a rate of 82.3 ml/hr. Water was produced by the system at a rate of 8.5 ml/hr and make-up sodium hydroxide solution was supplied to the aldol reactor at a rate of 81.6 ml/hr.

The aldehyde recycle column 123 was operated under conditions such that the feed temperature was 97.7° C., the reboiler temperature in reboiler 125 was 104.4° C. and the column head temperature was 87.9° C. The results obtained during this run are shown in Table 5.

TABLE 5

| | $C_5$-aldehyde feed in line 102 | Reactor Product in line 121 (Org Phase) (A) | Organic Product in line 173 (B) | Organic Reflux/Recycle in line 147 (C) |
|---|---|---|---|---|
| 2MBAL | 4.89 | 9.13 | 0.07 | 39.91 |
| NVAL | 94.89 | 10.76 | 0.35 | 48.58 |
| 2MBOL | ND | 0.70 | ND | 2.98 |
| Pentanol | ND | 1.30 | ND | 5.59 |
| Unknowns | ND | 0.20 | 0.02 | ND |
| iso-PBA | ND | 7.24 | 9.69 | 2.17 |
| PBA | ND | 66.20 | 88.84 | 0.54 |
| Aldols | ND | 3.00 | 0.14 | 0.09 |
| Lights | 0.05 | 0.04 | ND | 0.12 |
| Heavies | 0.16 | 1.43 | 0.89 | ND |

Notes:
1. 2MBAL = 2-methyl butyraldehyde
2. NVAL = n-valeraldehyde
3. 2MBOL = 2-methyl butanol
4. PBA = propyl butyl acrolein
5. iso-PBA = mixed $C_{10}$ acroleins (other than PBA)
6. ND = not detected.

Comparative Example A

In this Example the distillation column was operated in the absence of alkali. The distillation column was washed with deionised water until the washings had no effect on phenolphthalein indicator. Line 121 was temporarily disconnected from distillation column 123 and was connected downstream from valve 122 directly to separator vessel 161. Reactor vessel 111 was supplied at 150 ml/hour from line 102 with a $C_5$ aldehyde feed which was predominantly n-valeraldehyde (NVAL) containing 4.89% of 2-methylbutyraldehyde (2MBAL), 0.6% of "heavies" and a trace of low boiling materials. No recycle aldehyde was supplied in line 109. Sodium hydroxide solution (20.15 g/l) was supplied in line 110 at a rate of 151 ml/hour; no recycle stream was supplied in line 175. The volume of liquid in reactor 111 was 70 ml and the temperature therein was held at 120° C., the pressure being 140 psig (9.6 bar). The two phase liquid from let down valve 122 was collected in separator 161 and allowed to separate. The organic phase was passed by line 163 to vessel 164, and then via line 171, pump 172 and line 173 to nitrogen blanketed storage at room temperature. The composition of the material in line 171 was 2.5% 2MBAL, 11.5% NVAL, 4.0 aldols, 2.9% iso-PBA, 78.2% PBA and 0.9% "heavies". There were also traces of pentanols and "lights". After 12 hours in the storage vessel the composition had the following analysis: 2.41% 2MBAL, 5.59% NVAL, 6.93% aldols, 2.9% iso-PBA, 80.55% PBA, and 1.6% "heavies", along with traces of pentanols and "lights". The increase in aldol content indicates that aldolisation is continuing on storage, possibly due to residual traces of alkali in the organic phase.

The normal connections at the base of the distillation column 123 were reestablished. The stirred product was fed to the washed distillation column 123 from upstream of valve 122 at a rate of 150 ml/hour, together with 150 ml/hour of deionised water. The temperature at the feed point for this mixture was 98° C., the temperature in the reboiler 125 was 100.1° C., and the overhead temperature in line 128 was 87.1° C. The flow rate in line 146 was 70 ml/hour and that in line 153 was 10 ml/hour. The balance of the organic overhead product was recovered in line 109 (which was disconnected from line 108) at a rate of 6–10 ml/hour. The water recovery rate in line 156 was 10 ml/hour. Water was discharged from time to time from separator 169 which had been disconnected from line 174.

The materials in lines 173 and 146 had the analysis of Table 6:

TABLE 6

| Line No. | (Concentration (%)) | |
|---|---|---|
| | 173 | 146 |
| 2MBAL | 1.91 | 31.10 |
| NVAL | 2.15 | 68.35 |
| Pentanol | ND | Trace |
| Unknowns | ND | Trace |
| iso-PBA | 2.78 | 0.51 |
| PBA | 84.46 | 0.04 |
| Aldols | 7.01 | Trace |
| "Lights" | ND | Trace |
| "Heavies" | 1.69 | ND |

TABLE 7-continued

| Example No. | 5 | 6 | 7 | 8 |
|---|---|---|---|---|
| Line 110 | 152.00 | 151.00 | 154.00 | 150.00 |
| Line 153 | 20.00 | 8.00 | 22.00 | 15.00 |
| Line 181 | 84.70 | 84.00 | 82.30 | very low 3 |
| Line 184 | 81.26 | 82.18 1 | 81.32 2 | 3.00 |
| Line 156 | 6.00 | 6.50 | 7.80 | 12.40 |
| Caustic liquors (NaOH g/l) | | | | |
| Line 181 | 35.68 | 18.80 | 18.48 | 19.00 |
| Line 184 | 38.56 | 19.68 | 19.36 | 20.00 |
| Caustic consumed: (g/hr) | 0.11 | 0.04 | 0.05 | 0.06 |
| Column conditions | | | | |
| Head temp. °C. | 88.0 | 87.7 | 88.5 | 87 |
| Feed temp. °C. | 98.0 | 98.1 | 96.8 | 95 |
| Reboiler temp. °C. | 100.3 | 100.4 | 100.7 | 102 |

Notes:
1. 19.68 g/l NaOH plus 89.4 g/l sodium butyrate.
2. 19.36 g/l NaOH plus 155 g/l sodium butyrate
3. Sodium valerate concentration in aqueous phase accumulated to 75 g/l over a 150 hour run; the results are given at the end of the run when the sodium valerate had reached these levels.

The composition of the various streams was as set out in Table 8.

TABLE 8

| | STREAM ANALYSIS (MOL %) | | | | | | | | | | | | | | | |
|---|---|---|---|---|---|---|---|---|---|---|---|---|---|---|---|---|
| | EXAMPLE 5 Line (FIG. 2) | | | | EXAMPLE 6 Line (FIG. 2) | | | | EXAMPLE 7 Line (FIG. 2) | | | | EXAMPLE 8 Line (FIG. 2) | | | |
| | 121 | 173 | 138 | 156* | 121 | 173 | 138 | 156* | 121 | 173 | 138 | 156* | 121 | 173 | 138 | 156* |
| 2MBAL | 9.18 | 0.04 | 42.13 | 0.52 | 11.12 | 0.04 | 41.09 | 0.35 | 10.01 | 0.05 | 40.04 | 0.53 | 9.20 | 0.11 | 39.80 | 0.71 |
| NVAL | 8.72 | 0.21 | 46.30 | 0.70 | 11.83 | 0.29 | 50.35 | 0.66 | 11.73 | 0.46 | 47.46 | 0.82 | 10.81 | 0.52 | 48.55 | 1.03 |
| 2MBOL | 0.52 | ND | 2.19 | 0.09 | 0.63 | ND | 2.31 | 0.10 | 0.68 | ND | 2.89 | 0.12 | 0.70 | 0.00 | 2.80 | 0.11 |
| $C_5OL$ | 0.94 | ND | 4.04 | 0.13 | 1.11 | ND | 3.96 | 0.15 | 1.24 | ND | 5.22 | 0.18 | 1.28 | ND | 5.60 | 0.19 |
| Unks. | 0.06 | 0.02 | ND | | 0.10 | 0.03 | 0.05 | | 0.07 | 0.04 | trace | | 0.19 | 0.12 | trace | |
| iso-PBA | 8.46 | 10.13 | 3.01 | | 7.38 | 9.83 | 1.40 | | 7.46 | 9.70 | 2.35 | | 7.26 | 9.68 | 1.89 | |
| PBA | 68.23 | 58.39 | 1.47 | | 64.19 | 86.26 | 0.44 | | 65.30 | 88.04 | 1.63 | | 66.22 | 88.76 | 1.04 | |
| Aldols | 2.73 | 0.14 | | | 2.57 | 0.06 | 0.09 | | 2.08 | 0.03 | 0.25 | | 3.15 | 0.02 | 0.25 | |
| Lights | 0.23 | ND | 0.86 | trace | 0.09 | ND | 0.29 | trace | 0.05 | ND | 0.16 | trace | 0.05 | 0.00 | 0.08 | trace |
| Heavies | 0.94 | 1.07 | ND | | 0.97 | 1.50 | ND | trace | 1.38 | 1.70 | ND | | 1.14 | 0.90 | ND | |

Notes:
ND = Not detected by gas-liquid chromatography
2MBAL = 2-methyl butyraldehyde
NVAL = n-valeraldehyde
2MBOL = 2-methyl butanol
PBA = propyl butyl acrolein
isoPBA = mixed $C_{10}$ acroleins other than PBA
* = the values given for line 156 are in each case in wt. %

This Comparative Example shows clearly that it is essential to have an aldolisation catalyst, e.g. sodium hydroxide catalyst, in the lower, higher temperature part of the distillation zone. The high residual aldol content in the organic product in line 173 in this Comparative Example, coupled with the unusually high aldehyde content in this organic product, shows that the lower part of the distillation column 123 is now not an effective converter of the aldolisation reactor intermediate products to $C_5$ aldehydes and/or $C_{10}$ acroleins.

EXAMPLES 5 TO 8

The apparatus of FIG. 2 was supplied with a $C_5$ aldehyde feed under a number of different conditions of feed rate, recycle rate, purge rate and distillation column temperatures. The specific conditions are set out in Table 7 below.

TABLE 7

| Example No. | 5 | 6 | 7 | 8 |
|---|---|---|---|---|
| Flow rates (ml/hr) | | | | |
| Line 102 | 109.00 | 102.00 | 107.00 | 110.00 |
| Line 146 | 20.00 | 26.00 | 74.00 | 50.00 |
| Line 109 | 41.00 | 53.00 | 48.00 | 40.00 |

The stream analysis from line 21 is obtained by withdrawing from line 21 a small aliquot of the mixed stream, allowing the aliquot to separate into an aqueous phase and an organic phase and performing the analysis on the organic phase.

What is claimed is:

1. A process for the production of substituted acroleins which comprises aldolisation of an aldehyde or a mixture of aldehydes in the presence of an effective amount of a water-soluble aldolisation catalyst followed by dehydration to form at least one substituted acrolein and water, recovering from the aldolisation/dehydration step a reaction mixture comprising unreacted aldehyde or aldehydes, water, aldolisation catalyst, and said at least one substituted acrolein, and distilling the reaction mixture to separate (i) an overhead fraction comprising unreacted aldehyde or aldehydes and water from (ii) a bottoms fraction containing said aldolisation catalyst and said at least one substituted acrolein, recycling unreacted aldehyde or aldehydes of said overhead fraction to the aldolisation/dehydration step, and purging from the system a stream substantially free from said aldolisation catalyst and comprising water from said overhead fraction.

2. A process according to claim 1, in which the aldehyde or each of the aldehydes contains from 3 to 10 carbon atoms.

3. A process according to claim 1 in which the aldolisation catalyst is an alkali metal hydroxide or carbonate or an alkaline earth metal hydroxide.

4. A process according to claim 1, in which the aldolisation catalyst is selected from sodium hydroxide, sodium carbonate, potassium hydroxide, and potassium carbonate.

5. A process according to claims 1, in which the aldolisation step is carried out at a temperature in the range of from about 80° C. to about 150° C. and at a pressure of from about 0.1 bar to about 10 bar.

6. A process according to claim 1, in which the distillation step is conducted at a pressure of from about 0.1 bar to about 2 bar.

7. A process according to claim 1, in which the overhead fraction is condensed and allowed to separate to form an upper organic phase containing unreacted aldehyde or aldehydes and a lower water phase.

8. A process according to claim 7, in which a part of the lower water phase is returned to the distillation step as a reflux stream.

9. A process according to claim 7, in which a part of the upper organic phase is recycled to the distillation step as a reflux stream.

10. A process according to claim 7, in which a part of the upper organic phase is purged from the plant in order to control the build up of volatile non-aldehyde materials in the process.

11. A process according to claim 1, in which the bottoms fraction from the distillation step is cooled and allowed to separate into an upper organic phase rich in substituted acrolein and a lower catalyst containing phase.

12. A process according to claim 11, in which lower catalyst containing phase is recycled to the aldolisation/dehydration step.

13. A process according to claim 12, in which a part of the lower catalyst containing phase is purged from the process in order to control the build up of Cannizzaro reaction products and in which an amount of make up aldolisation catalyst corresponding to any metal ions lost in the purge stream is supplied to the aldolisation step.

14. A process according to claim 11, in which the lower catalyst containing phase contains from about 0.1% w/v to about 5% w/v of aldolisation catalyst and up to about 35% w/v of a salt or salts of an organic acid or acids produced by Cannizzaro reactions.

15. A process according to claim 1, in which aldolisation is effected in a stirred tank reactor provided with internal baffles.

16. A process according to claim 1, in which aldolisation is carried out in an aldolisation zone with a residence time of from about 2 minutes to about 75 minutes.

17. A process according to claim 1, in which aldolisation is carried out with an organic phase:aqueous phase ratio of from about 3:1 to about 1:15 by volume.

18. A process according to claim 1, in which aldolisation is carried out in a tank reactor provided with a stirrer and in which the power supplied to the stirrer ranges from about 1.0 to about 3.0 kW/m³ of liquor.

19. A process according to claim 1, in which the aldolisation/dehydration step is effected using a mixture of $C_5$ aldehydes which comprises at least 88 molar % of n-valeraldehyde, not more than 10 molar % of 2-methylbutyraldehyde, and not more than 2 molar % of 3-methylbutyraldehyde and in which the bottoms fraction from the distillation step contains less than 0.3% w/v of aldols.

20. A process according to claim 19, in which the mixture of $C_5$ aldehydes contains at least 94 molar % of n-valeraldehyde, not more than 5 molar % of 2-methylbutyraldehyde, and not more than 1 molar % of 3-methylbutyraldehyde and in which the bottoms fraction from the distillation step contains less than 0.3% w/v of aldols.

21. A process according to claim 19 in which the mixture of aldehydes contains at least 98.8 molar % of n-valeraldehyde, not more than 1.2 molar % 2-methylbutyraldehyde, and not more than 0.01 molar % 3-methylbutyraldehyde and in which the bottoms fraction from the distillation step contains less than 0.3% w/v of aldols.

22. A continuous process for aldolisation of an aldehyde followed by dehydration to form a substituted acrolein containing twice as many carbon atoms as said aldehyde, which process comprises:
   (a) providing an aldolisation zone and a distillation zone;
   (b) continuously supplying to the aldolisation zone an organic stream containing said aldehyde and an aqueous stream containing an alkali catalyst;
   (c) maintaining said aldolisation zone under aldolisation and dehydration conditions effective for conversion of said aldehyde in the presence of said alkali catalyst to an aldolisation product with subsequent dehydration of said aldolisation product to form said substituted acrolein;
   (d) recovering from said aldolisation zone a reaction product stream comprising mixed organic and aqueous phases;
   (e) distilling said reaction product stream in said distillation zone;
   (f) recovering overhead from said distillation zone a vaporous stream comprising unreacted aldehyde and water;
   (g) condensing said vaporous stream;
   (h) allowing the resulting condensate to separate into an upper organic phase and a lower water phase;
   (i) purging at least a part of said lower water phase;
   (j) recycling material of said upper organic phase to said aldolisation zone;
   (k) recovering from a bottom part of said distillation zone a bottoms product comprising an organic phase rich in substituted acrolein and an aqueous phase containing said alkali catalyst;
   (l) cooling said bottoms product;
   (m) allowing said cooled bottoms product to separate into an upper organic phase rich in substituted acrolein and a lower catalyst containing phase;
   (n) recycling material of said lower catalyst containing phase to said aldolisation zone; and
   (o) recovering said upper organic phase of step (m).

23. A process according to claim 22, in which said aldehyde is selected from aldehydes containing from 3 to 10 carbon atoms and mixtures thereof.

24. A process according to claim 22, in which said alkali catalyst is selected from sodium hydroxide, sodium carbonate, potassium hydroxide, and potassium carbonate.

25. A process according to claim 22, in which the aldolisation zone is maintained at a temperature in the range of from about 80° C. to about 150° C. and at a pressure of from about 0.5 to about 10 bar.

26. A process according to claim 22 in which the distillation zone is operated at a pressure of from about 0.1 bar to about 2 bar.

27. A process according to claim 22 in which a part of the lower water phase of step (h) is recycled to the distillation zone as a reflux stream.

28. A process according to claim 22 in which a part of the upper organic phase of step (h) is recycled to the distillation zone as a reflux stream.

29. A process according to claim 22 in which a part of the lower catalyst phase of step (m) is purged from the plant to control the build up of Cannizzaro reaction products and in which an amount of alkali catalyst corresponding to any metal ions lost by purging is supplied to the aldolisation zone.

30. A process according to claim 22 in which the aldolisation zone comprises a stirred tank reactor provided with internal baffles.

31. A process according to claim 22 in which the residence time in the aldolisation zone ranges from about 2 minutes to about 75 minutes.

32. A process according to claim 22 in which the organic phase:aqueous phase ratio in the aldolisation zone ranges from about 3:1 to about 1:15 by volume.

33. A process according to claim 22, in which the aqueous stream supplied to the aldolisation zone in step (b) comprises from about 0.1% w/v to about 5% w/v of sodium hydroxide and up to about 35% w/v of sodium salts of organic acids produced by Cannizzaro reactions.

34. A process according to claim 22, in which the aldolisation zone comprises a stirred tank reactor operated under aqueous continuous phase conditions.

35. A process according to claim 22, in which the aldolisation zone comprises a stirred tank reactor and in which the power supplied to the stirrer ranges from about 1.0 to about 3.0 kW/m$^3$ of liquor.

36. A process according to claim 22, in which a part of the upper organic phase of step (h) is purged from the plant in order to control the build up of volatile non aldehyde materials in the plant.

37. A process according to claim 22 in which the aldehyde is supplied to the aldolisation step in the form of a mixture of isomeric aldehydes.

38. A process according to claim 22, in which the aldolisation zone is supplied with a mixture of C$_5$ aldehydes which comprises at least 88 molar % of n-valeraldehyde, not more than 10 molar % of 2-methylbutyraldehyde, and not more than 2 molar % of 3-methylbutyraldehyde and in which the bottoms product of step (k) contains less than 0.3% w/v of aldol or aldols.

39. A process according to claim 38, in which the mixture of C$_5$ aldehydes contains at least 94 molar % of n-valeraldehyde, not more than 5 molar % of 2-methylbutyraldehyde, and not more than 1 molar % of 3-methylbutyraldehyde and in which the bottoms product of step (k) contains less than 0.3% w/v of aldol or aldols.

40. A process according to claim 38, in which the mixture of aldehydes contains at least 98.8 molar % of n-valeraldehyde, not more than 1.2 molar % 2-methylbutyraldehyde, and not more than 0.01 molar % 3-methylbutyraldehyde and in which the bottoms product of step (k) contains less than 0.3% w/v of aldol or aldols.

41. A process for the production of substituted acroleins which comprises contacting an aldehyde or mixture of aldehydes under aldolisation and dehydration conditions with an effective amount of an aldolisation catalyst thereby to form by aldolisation/dehydration a reaction mixture comprising unreacted aldehyde or aldehydes, aldols, water, aldolisation catalyst, at least one substituted acrolein, and "heavies", supplying resulting reaction mixture to an intermediate section of a distillation zone which further includes a higher temperature section below said intermediate section and also a lower temperature distillation section, maintaining distillation conditions in the higher temperature section effective for decomposition of aldols and "heavies" in the presence of the aldolisation catalyst, recovering aldehyde or aldehydes from the lower temperature section for recycle to the aldolisation/dehydration step, and recovering from the higher temperature section a bottoms fraction comprising substituted acrolein and aldolisation catalyst.

42. A C$_{10}$ substituted acrolein mixture which comprises (i) at least 88 molar % 2-propylhept-2-enal, (ii) not more than 10 molar: % 2-propyl-4-methylhex-2-enal, and ( iii ) not more than 2 molar % in total of 2-propyl-5-methylhex-2-enal, 2-iso-propylhept-2-enal, 2-iso-propyl-5-methylhex-2-enal, and 2-iso-propyl-4-methylhex-2-enal.

43. A C$_{10}$ substituted acrolein mixture which comprises (i) at least 76 molar % 2-propylhept-2-enal, (ii) not more than 20 molar % 2-propyl-4-methylhex-2-enal, and (iii) not more than 4 molar % in total of 2-propyl-5-methylhex-2-enal, 2-iso-propylhept-2-enal, 2-iso-propyl-5-methylhex-2-enal, and 2-iso-propyl-4-methylhex-2-enal.

44. A C$_{10}$ substituted acrolein mixture which comprises (i) at least 97.6 molar % 2-propylhept-2-enal, (ii) not more than 2.4 molar % 2-propyl-4-methylhex-2-enal and (iii) not more than 0.01 molar % in total of 2-propyl-5-methylhex-2-enal, 2-iso-propylhept-2-enal, 2-iso-propylhept-2-enal, 2-iso-propyl-5-methylhex-2-enal, and 2-iso-propyl-4-methylhex-2-enal.

45. A C$_{10}$ substituted acrolein mixture which comprises (i) at least 95.8 molar % 2-propylhept-2-enal, (ii) not more than 4.0 molar % 2-propyl-4-methylhex-2-enal, and (iii) not more than 0.2 molar % 2-propyl-5-methylhex-2-enal, 2-iso-propylhept-2-enal, 2-iso-propyl-5-methylhex-2-enal, and 2-iso-propyl-4-methylhex-2-enal.

* * * * *

UNITED STATES PATENT AND TRADEMARK OFFICE
CERTIFICATE OF CORRECTION

PATENT NO. : 5,434,313

DATED : July 18, 1995

INVENTOR(S) : George E. Harrison et al.

It is certified that error appears in the above-indentified patent and that said Letters Patent is hereby corrected as shown below:

Col. 2, lines 21-22: the formula should be -- $2R.CH_2.CHO + NaOH \rightarrow R.CH_2.COONa + R.CH_2.CH_2.OH$ --; Col. 5, line 59, delete the colon; Col. 10, lines 20-22, the formula should be --
$$\begin{array}{c} CH_3.CH_2.CH_2.CH_2.CH \\ \| \\ CH_3.CH.C.CHO \\ | \\ CH_3 \end{array}$$
--; Col. 10, line 39, after "up to" insert -- 98% --; Col. 11, line 9, "16 g" should be -- 16 a --; Col. 19, line 7, "$C_{10}$-primary" should be -- $C_{10}$ primary --; Col. 22, line 32, after "column" insert -- 123 --; Cols. 23-24, Table 8, under the "EXAMPLE 6 Line (FIG. 2)" column, subcolumn "173", the seventh entry designated for the row "PBA", should be changed from "86.26" to -- 88.26 --; Col. 23, lines 58-59, "$C_5$aldehyde" should be -- $C_5$-aldehyde --;  Col. 25, line 6 (claim 3), after

UNITED STATES PATENT AND TRADEMARK OFFICE
CERTIFICATE OF CORRECTION

PATENT NO. : 5,434,313  
DATED : July 18, 1995  
INVENTOR(S) : George E. Harrison et al.

Page 2 of 2

It is certified that error appears in the above-indentified patent and that said Letters Patent is hereby corrected as shown below:

```
"claim 1" insert a comma; Col. 25, line 13 (claim 5), "claims 1"
should be -- claim 1 --; Col. 26, line 14 (claim 21), after
"claim 19" insert a comma; Col. 27, line 5 (claim 26), after
"claim 22" insert a comma; Col. 27, line 8 (claim 27), after
"claim 22" insert a comma; Col. 27, line 11 (claim 28), after
"claim 22" insert a comma; Col. 27, line 14 (claim 29), after
"claim 22" insert a comma; Col. 27, line 20 (claim 30), after
"claim 22" insert a comma; Col. 27, line 23 (claim 31), after
"claim 22" insert a comma; Col. 27, line 26 (claim 32), after
"claim 22" insert a comma; Col. 27, line 46 (claim 37), after
"claim 22" insert a comma; Col. 28, line 34 (claim 42), delete
the colon.
```

Signed and Sealed this

Twentieth Day of February, 1996

Attest:

BRUCE LEHMAN

Attesting Officer

Commissioner of Patents and Trademarks